United States Patent
Agrawal et al.

(10) Patent No.: US 9,891,958 B2
(45) Date of Patent: Feb. 13, 2018

(54) SYSTEM AND METHOD FOR PARALLELIZING GRID SEARCH METHOD FACILITATING DETERMINATION OF PK-PD PARAMETERS

(71) Applicant: Tata Consultancy Services Limited, Mumbai, Maharashtra (IN)

(72) Inventors: Nishant Kumar Agrawal, Maharashtra (IN); R. Narayanan, Andhra Pradesh (IN); Manoj Karunakaran Nambiar, Maharashtra (IN); Rihab Abdulrazak, Maharashtra (IN); Ambuj Pandey, Maharashtra (IN); Shyam Sundar Das, Andhra Pradesh (IN)

(73) Assignee: Tata Consultancy Services Limited, Mumbai, Maharashtra (IN)

( * ) Notice: Subject to any disclaimer, the term of this patent is extended or adjusted under 35 U.S.C. 154(b) by 323 days.

(21) Appl. No.: 14/663,968

(22) Filed: Mar. 20, 2015

(65) Prior Publication Data
US 2015/0269225 A1    Sep. 24, 2015

(30) Foreign Application Priority Data
Mar. 21, 2014    (IN) .......................... 934/MUM/2014

(51) Int. Cl.
G06F 17/30    (2006.01)
G06F 9/50    (2006.01)
G06F 19/00    (2011.01)

(52) U.S. Cl.
CPC ...... *G06F 9/5044* (2013.01); *G06F 17/30864* (2013.01); *G06F 17/30867* (2013.01); *G06F 19/709* (2013.01); *G06F 19/704* (2013.01)

(58) Field of Classification Search
CPC ......... G06F 17/30864; G06F 17/30867; G06F 9/5044; G06F 19/704; G06F 19/709; G06Q 30/02
(Continued)

(56) References Cited

U.S. PATENT DOCUMENTS

| | | | |
|---|---|---|---|
| 8,650,017 B2* | 2/2014 | Kirnasovsky ...... | G01N 33/5011 702/19 |
| 2007/0054331 A1* | 3/2007 | Kirnasovsky ...... | G01N 33/5011 702/19 |

(Continued)

OTHER PUBLICATIONS

Hairong GU, M.S.; "Graphic-Processing-Units Based Adaptive Parameter Estimation of a Visual Psychophysical Model"; Thesis Presented at The Ohio State University 2012.

*Primary Examiner* — Shahid Alam
(74) *Attorney, Agent, or Firm* — Merchant & Gould P.C.

(57) ABSTRACT

Disclosed is a system and method for parallelizing grid search technique facilitating determination of PK-PD parameters. The method may comprise determining number of grids. The method may further comprise creating grid points based upon the number of grids (N) and a number of parameters (p). The method may further comprise distributing the grid points amongst number of threads. The method may further comprise evaluating an objective function value corresponding to each grid point in order to compute an objective function value associated with each of the grid points. Further, the method may comprise identifying a grid point having minimum objective function value. The grid point having the least objective function value may indicate the estimated initial PK-PD parameters.

12 Claims, 11 Drawing Sheets

(58) Field of Classification Search
USPC .......................................................... 707/769
See application file for complete search history.

(56) References Cited

U.S. PATENT DOCUMENTS

| | | |
|---|---|---|
| 2007/0239416 A1 | 10/2007 | Saito et al. |
| 2014/0172765 A1* | 6/2014 | Williams ................ G06F 17/17 706/46 |
| 2015/0100286 A1* | 4/2015 | Williams ................ G06F 19/12 703/2 |

* cited by examiner

SYSTEM AND METHOD FOR PARALLELIZING GRID SEARCH METHOD FACILITATING DETERMINATION OF PK-PD PARAMETERS

CROSS-REFERENCE TO RELATED APPLICATIONS AND PRIORITY

The present application claims priority to Indian Patent Application No. 934/MUM/2014, filed on Mar. 21, 2014, the entirety of which is hereby incorporated by reference.

TECHNICAL FIELD

The present disclosure described herein, in general, relates to high performance computing and more particularly to a system and method of parallel implementation of grid search technique for determining initial PK-PD parameters.

BACKGROUND

Developability of a drug candidate is decided based on the Pharmacokinetic (PK) and Pharmacodynamic (PD) parameters of the drug candidate, usually estimated using Plasma Concentration Time (PCT) and effect-concentration profiles of the drug candidate, measured in a number of targeted animal/Human in vivo studies. PK is the study of what the body does to a drug, i.e., its absorption, distribution, metabolism and excretion profiles. PK modeling characterizes the blood or plasma concentration-time profiles following administration of a drug via various routes. On the other hand PD defines what a drug does to the body. PD modeling attempts to characterize measured physiological parameters before and after drug administration with the effect defined as the change in parameter relative to pre-dose or baseline value.

The objective of these models is to estimate the PK/PD parameters which is an integral part of model based drug development. The significance of accurately estimating these parameters lies in the fact that many of these parameters cannot be measured experimentally either in human or in animal. Further, the decision to take the compound/drug to the next level of drug development process depends heavily on the accuracy of the parameters values. The accuracy of the optimized parameter estimates obtained using available computing methods such as Gauss-Newton etc, is dependent on appropriate selection of initial parameter values. These estimations may be an educated guess based on the structure of the model, or may be determined by using estimated parameters from previous studies. However, these approaches do not always guarantee good initial estimates of all the PK-PD parameters of interest. Further, the number of parameters and complexity of the model increase the execution time required for a computing method to estimate the parameters.

SUMMARY

This summary is provided to introduce aspects related to systems and methods for searching PK-PD parameters in a parameter space and the concepts are further described below in the detailed description. This summary is not intended to identify essential features of subject matter nor is it intended for use in determining or limiting the scope of the subject matter.

In one implementation, a system for searching the PK-PD parameters in the parameter space is disclosed. The system may comprise a processor and a memory coupled to the processor for executing a plurality of modules stored in the memory. The plurality of modules may comprise a receiving module, a determining module, and a computing module. The receiving module may receive a number of grids (N) induced over a parameter space, number of parameters (p), lower bound value (LBi) and upper bound value (UBi) of each parameter. Further, the determining module may determine total number of grid points (n) based upon the number of grids (N) and the number of parameters (p). Further, each grid point of the total number of grid points is separated from an adjacent grid point based upon a step size. Further, each of the total number of grid points (n) is represented by a set of coordinates. Further, the computing module may compute plurality of grid points corresponding to the set of coordinates associated therewith based on the lower bound value (LBi), the upper bound value (UBi), and the number of grids (N). The computing module may further parallelly compute an objective function value for each grid point of the plurality of grid points. Further, a grid point having a minimum objective function value indicates the PK-PD parameters.

In another implementation, a method for searching the PK-PD parameters in parameter space is disclosed. The method may comprise receiving, by a processor, a number of grids (N) induced over a parameter space, number of parameters (p), lower bound value (LBi) and upper bound value (UBi) of each parameter. The method may further comprise a step of determining, by the processor, total number of grid points (n) based upon the number of grids (N) and the number of parameters (p). Further, each grid point of the total number of grid points is separated from an adjacent grid point based upon a step size. Further, each of the total number of grid points (n) is represented by a set of coordinates. Further, the method may comprise a step of computing, by the processor, plurality of grid points corresponding to the set of coordinates associated therewith based upon the lower bound value (LBi), the upper bound value (UBi), and the number of grids (N). The method may further comprise a step of parallelly computing, by the processor, an objective function value for each grid point of the plurality of grid points. Further, a grid point having a minimum objective function value indicates the PK-PD parameters.

In yet another implementation, a non-transitory computer readable medium embodying a program executable in a computing device for searching PK-PD parameters in a parameter space is disclosed. The program comprising a program code for receiving a number of grids (N) induced over a parameter space, number of parameters (p), lower bound value (LBi) and upper bound value (UBi) of each parameter. The program may further comprise a program code for determining total number of grid points (n) based upon the number of grids (N) and the number of parameters (p). Further, each grid point of the total number of grid points is separated from an adjacent grid point based upon a step size. Further, each of the total number of grid points (n) is represented by a set of coordinates. Further, the program may comprise a program code for computing plurality of grid points corresponding to the set of coordinates associated therewith based upon the lower bound value (LBi), the upper bound value (UBi), and the number of grids (N). The program may further comprise a program code for parallelly computing an objective function value for each grid point of the plurality of grid points. Further, a grid point having a minimum objective function value indicates the PK-PD parameters.

BRIEF DESCRIPTION OF THE DRAWINGS

The foregoing detailed description of embodiments is better understood when read in conjunction with the appended drawings. For the purpose of illustrating the disclosure, there is shown in the present document example constructions of the disclosure; however, the disclosure is not limited to the specific methods and systems disclosed in the document and the drawings.

The detailed description is described with reference to the accompanying figures. In the figures, the left-most digit(s) of a reference number identifies the figure in which the reference number first appears. The same numbers are used throughout the drawings to refer like features and components.

FIG. 3 (b) illustrates a graphical plot depicting the observed Vs estimated/predicated plasma concentration-time profile, in accordance with an embodiment of the present disclosure.

FIG. 4 (b) is a graphical plot illustrating the relationship between the number of explorations and number of grid points, in accordance with an embodiment of the present disclosure.

FIG. 5 (b) is a graphical plot illustrating performance of the grid search technique implemented using the OpenMP, in accordance with an embodiment of the present disclosure.

FIG. 6 (b) illustrates a parallel grid search technique using MPI-OpenMP computation, in accordance with an embodiment of the present disclosure.

FIG. 7 (b) illustrates a parallel grid search technique using GPU computation, in accordance with an embodiment of the present disclosure.

DETAILED DESCRIPTION

Systems and methods for searching or estimating PK-PD parameters in a parameter space are described. The present disclosure facilitates parallel implementation of grid search technique for determining the PK-PD parameters or initial PK-PD parameters. The present disclosure also discloses about implementing the parallelized grid search method on shared memory system (using OpenMp—Open Multi-Processing) and distributed memory system (using MPI—Message passing Interface and GPU—Graphics Processing Unit). Each of this implementation is discussed in detail in subsequent paragraphs of the specification.

Further, the parallel implementation of the grid search technique provides faster solution to time-consuming PK-PD parameter estimation problem in case of a number of scenarios. Parallelizing serial version of the application on GPU architecture may help in achieving high performance i.e. to reduce the overall execution time. The present disclosure may enable leveraging hardware architecture capabilities for high performance. A substantial improvement in execution time may be observed as a result of the parallel implementation. In accordance with the present disclosure, robust estimation of PK-PD parameters is proposed by a two-step approach, involving the estimation of initial PK-PD parameters followed by optimization to final PK-PD parameters estimates with minimum objective function value.

According to embodiments of present disclosure, the two step approach includes employing parallelized Grid search method and/or technique on the GPU for the estimation of the initial PK-PD parameters (Step 1) thereby providing robust final estimates, following optimization using optimization methods such as Gauss-Newton, Nelder-Mead etc, in case of a number of pre-defined—PK-PD models. Significantly, a uniform bound of PK-PD parameters, may be used as an input data for the parallelized Grid Search method and there is no precedence to the use of such an approach in the literature. The uniform PK-PD parameters bound (Parameter space) may be identified based on the parameter space of the marketed drugs and/or some other rationale. It is expected that new drug candidates that have PK-PD parameters within the parameter space is likely to have developability potential. Such an approach, if successful may have potential to minimize or completely remove the role of subject matter experts (SMEs) or inputs received from the SMEs.

While aspects of described system and method for searching the PK-PD parameters in the parameter space by parallelizing the grid search technique may be implemented in any number of different computing systems, environments, and/or configurations, the embodiments are described in the context of the following exemplary system.

Figure 1:
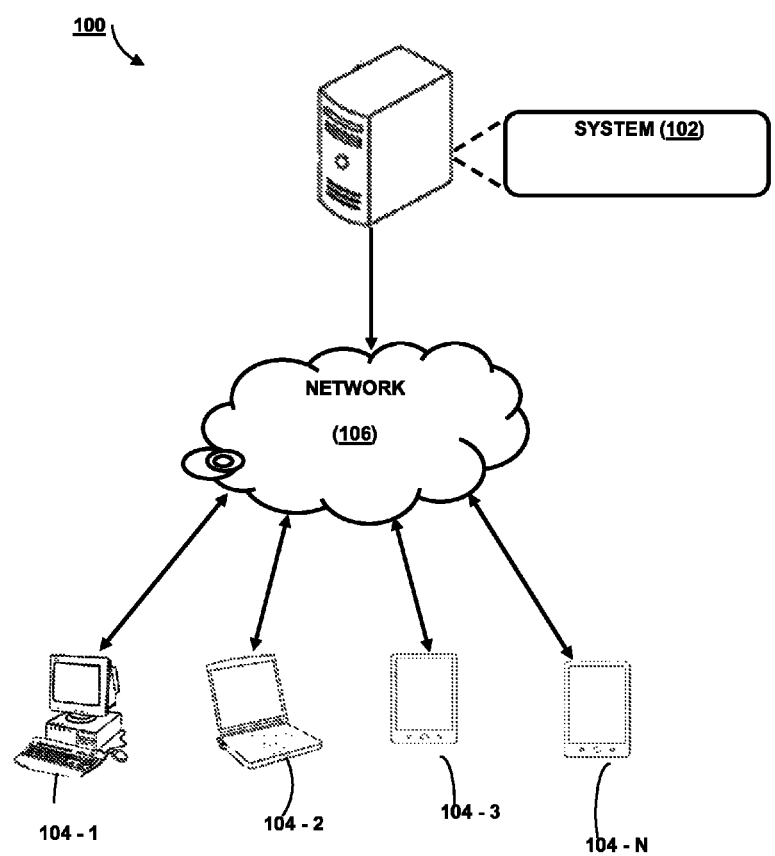
FIG. 1 illustrates a network implementation of a system for searching PK-PD parameters in a parameter space, in accordance with an embodiment of the present disclosure.

Referring to FIG. 1, a network implementation 100 of a system 102 for searching the PK-PD parameters in the parameter space is illustrated, in accordance with an embodiment of the present subject matter. Although the present subject matter is explained considering that the system 102 is implemented on a server, it may be understood that the system 102 may also be implemented in a variety of computing systems, such as a laptop computer, a desktop computer, a notebook, a workstation, a mainframe computer, a cloud-based computing environment and the like. It will be understood that the system 102 may be accessed by multiple users through one or more user devices 104-1, 104-2 . . . 104-N, collectively referred to as user devices 104 hereinafter, or applications residing on the user devices 104. In one implementation, the system 102 may comprise the cloud-based computing environment in which a user may operate individual computing systems configured to execute remotely located applications. Examples of the user devices 104 may include, but are not limited to, a portable computer, a personal digital assistant, a handheld device, a workstation and the like. The user devices 104 are communicatively coupled to the system 102 through a network 106.

In one implementation, the network 106 may be a wireless network, a wired network or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 106 may include a variety of network devices, including routers, bridges, servers, computing devices, storage devices, and the like.

Figure 2:
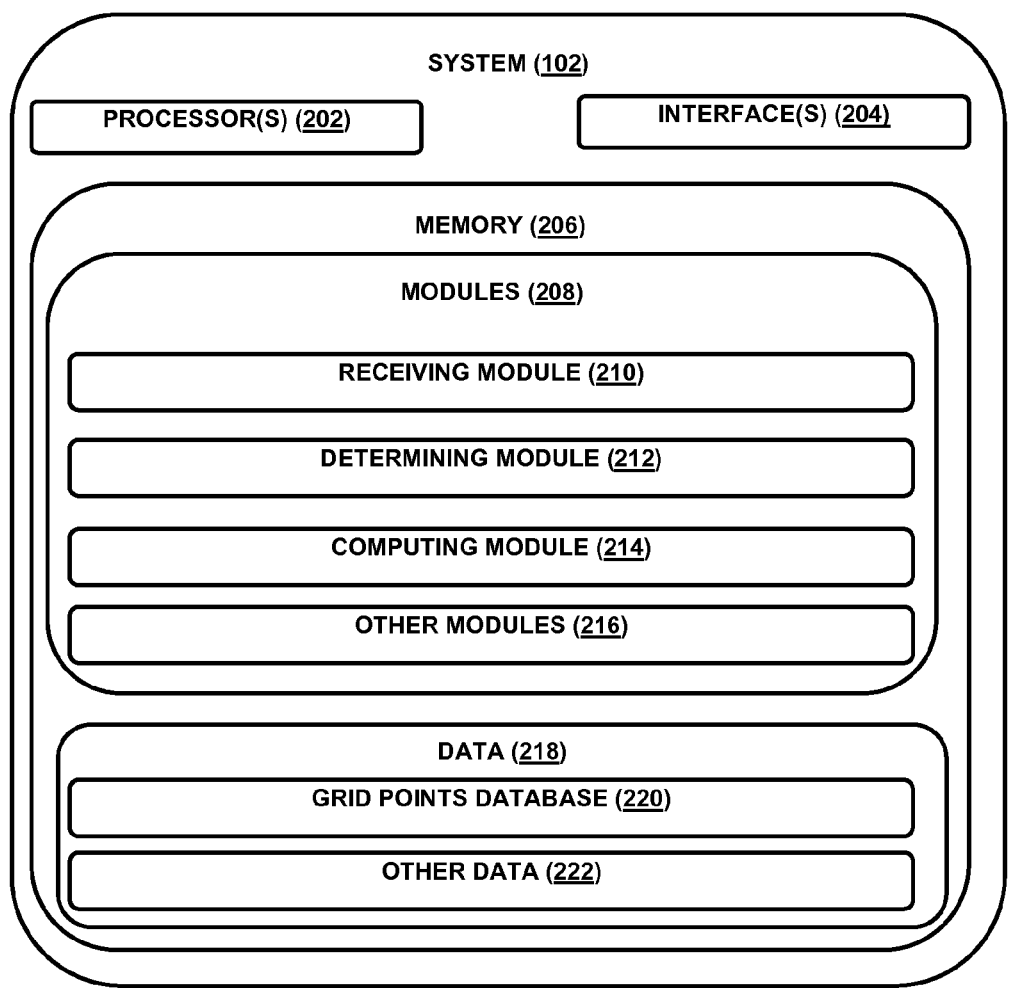
FIG. 2 illustrates the system, in accordance with an embodiment of the present disclosure.

Referring now to FIG. 2, the system 102 is illustrated in accordance with an embodiment of the present disclosure. In one embodiment, the system 102 may include one or more processors 202, an input/output (I/O) interface 204, and a memory 206. The processor(s) 202 may be implemented as microprocessors, microcomputers, microcontrollers, digital signal processors, central processing units, graphical processing units, state machines, logic circuitries, and/or any devices that manipulate signals based on operational instructions. Among other capabilities, the processor(s) 202 are configured to fetch and execute processor-executable instructions stored in the memory 206.

The I/O interface 204 may include a variety of software and hardware interfaces, for example, a web interface, a graphical user interface, and the like. The I/O interface 204 may allow the system 102 to interact with the user directly or through the user devices 104. Further, the I/O interface 204 may enable the system 102 to communicate with other computing devices, such as web servers and external data servers (not shown). The I/O interface 204 can facilitate multiple communications within a wide variety of networks and protocol types, including wired networks, for example, LAN, cable, etc., and wireless networks, such as WLAN, cellular, or satellite. The I/O interface 204 may include one or more ports for connecting a number of devices to one another or to another server.

The memory 206 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In one embodiment, the memory 206 may further include Graphics double data rate (GDDR) memory. The memory 206 may include modules 208, and data 218.

The modules 208 include routines, programs, objects, components, data structures, etc., which perform particular tasks or implement particular abstract data types. In one implementation, the modules 208 may include a receiving module 210, determining module 212, computing module 214, and other modules 216. The other modules 220 may include programs or coded instructions that supplement applications and functions of the system 102.

The data 218, amongst other things, serves as a repository for storing data processed, received, and generated by one or more of the modules 208. The data 218 may also include grid point database 220, and other data 222. The detail working of the system 102 is further described referring to FIGS. 3-8 as below.

According to embodiments of present disclosure, the system 102 may use compartmental models for searching or estimating PK-PD parameters in the parameter space. The compartmental models may assume a specific model structure and parameters for the model structure may be estimated from the experimentally observed data. The compartmental model may be a single or multi-compartmental model. According to other embodiments of present disclosure, the system 102 may also use different models other than the single and multi-compartmental models for searching or estimating the PK-PD parameters in the parameter space. The different models may be algebraic models and differential models. Further, the models may be selected based on various pharmacokinetic and pharmacodynamics applications requiring the estimation of the initial PK-PD parameters. Some of the examples of the applications along with the models selected for estimation are shown in table below.

| Pharmacokinetic Applications | Pharmacodynamic applications |
|---|---|
| One - compartment IV bolus dosing | One and two - site receptor binding |
| Two- compartment IV bolus dosing | Turnover model 1- Repeated dosing I |
| Intravenous and oral dosing | Effect Compartment III- Iv infusion |
| Two- compartment plasma and urine analysis with rate and ARE plots | Consecutive escalating infusions - Safety data |
| Bayesian model- Digoxin | Pool model of antilipolytic effect |

The above table illustrates few examples of the applications along with the models types. It should be noted to a person skilled in art that there be other applications available along with their respective models for estimating the initial PK-PD parameters.

Figure 3:
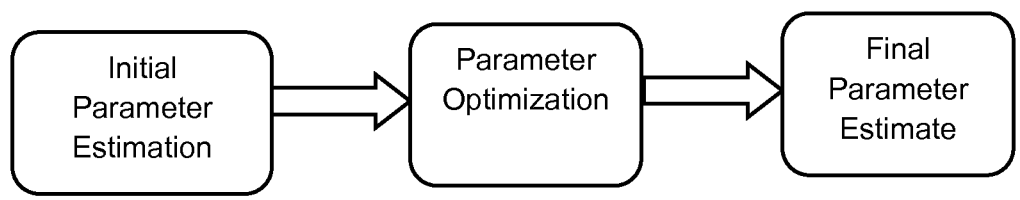
FIG. 3 (a) illustrates final parameter estimation approach for a PK/PD model, in accordance with an embodiment of the present disclosure.
Figure 3:
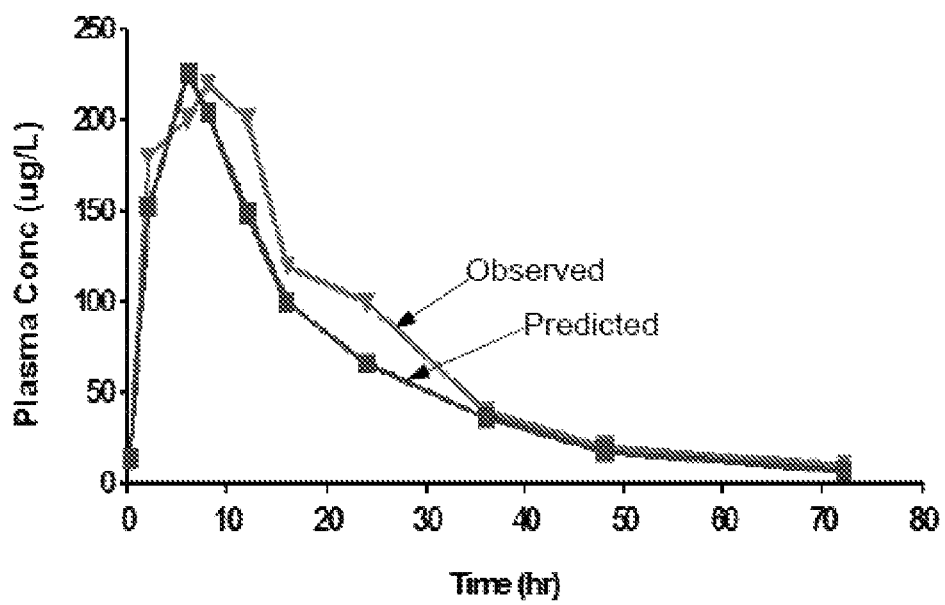

Referring to the FIG. 3(*a*), two main phases towards PK-PD parameter estimation is illustrated in detail. As shown in the FIG. 3(*a*), the two phases may include an initial parameter estimation phase and a parameter optimization phase. The initial parameter estimation step may be used to obtain initial parameter estimates for another optimization routine. Thus, the grid search technique may provide an initial rough estimate to an iterative optimization routine so that it may converge to an optimized value with minimum objective value (WSRS—Weighted Sum of Residual Square). As discussed earlier, it must be understood that better initial estimates of the parameters may result in faster convergence to the final parameter values with minimum objective value. Thus, the estimation of the initial PK-PD parameters is of primary importance.

Further, for estimating the initial PK-PD parameters, the grid search technique may be implemented by the system 102. The grid search technique—divides a parameter space into a number of grid points and compute an optimal grid point indicating the PK-PD parameter by performing an exhaustive search on all the—grid points (described in detail in subsequent paragraphs). The grid search technique chooses a grid point amongst the total number of grid points having a least value of objective function as the optimal grid point. Further, the grid points determined may be stored in the grid point database 220 of the system 102. While estimating the optimal grid point, it may be observed that, larger the number of grid points may result in better estimation. However, the total number of grid points to be searched in the parameter space may also increase exponentially. This may result in an exponential increase in execution time of the algorithm. Thus, to avoid such exponential increase, the system 102 discloses about implementing a parallel grid search technique/algorithm. The parallel implementations as well as various optimizations by the system 102 may facilitate in increase of the performance of the system 102. The performance is measured in terms of the total execution time of the execution of the parallel algorithm. In order to understand the working of the parallel algorithm, let us first understand a sequential grid search algorithm enabling the searching of the PK-PD parameters from the parameter space.

Referring to the FIG. 3(b), a graphical plot depicting an observed vs. estimated plasma concentration-time (PCT) profile is illustrated in detail. As can be seen from the FIG. 3(b), the observed data for the plasma concentration with time is available. In this case, the following three compartmental model used:

$$y(t) = Ae^{-\alpha t} + Be^{-\beta t} + Ce^{-\gamma t} \qquad (1)$$

wherein 'y(t)' is the plasma concentration, t is the time, and A, B, C, α, β, γ are parameters of the model. In accordance with some embodiments of the present disclosure, the above equation (1) may vary based upon the number of compartmental models. In the current case, the above equation (1) is derived corresponding to the three compartmental models. Therefore, one skilled in the art will readily realize that the equation (1) may be modified or updated based upon 'n' number of compartmental models which may be under consideration for the determining or estimating of the PK-PD parameters. The system 102 may determine a set of parameters for the model which best fits the data available. Amongst the set of parameters, the best fit is determined by calculating an objective function value for each of the set of parameters using following formula:

$$SRS = \sum_{i=1}^{\# \ Observations} (y_{observed}^{(i)} - y_{predicted}^{(i)})^2 \qquad (2)$$

In the above equation 2, $y_{observed}^{(t)}$ is observed value of dependent variable, and $y_{predicted}^{(t)}$ is predicted value obtained at the corresponding time by applying the model with the particular parameter values. If the objective function value (SRS) is less, the corresponding parameter values provide a better fit for the data. A more general form of the objective function value includes weights for particular observations, and accordingly modified formula is, $$WSRS = \sum_{i=1}^{\# \ Observations} w_i (y_{observed}^{(i)} - y_{predicted}^{(i)})^2 \qquad (3)$$

Where $w_i$ are the weights and $w_i$ may be 1, or $1/(y^{(i)}$ observed$)^\alpha$ or $1/(y^{(i)}$ predicted$)^\alpha$ where a is a natural number. Sometimes weights may be scaled so that $\Sigma w_i = 1$.

The optimized parameter value will be any value between the user-defined upper and the lower bounds of the parameter values. Thus, the system 102 may be configured to locate the parameter values between the upper bound value and the lower bound value with a minimum objective function. As disclosed above, the system 102, via implementing the grid search technique, may divide each of the parameter values into a number of grid points (n).

Figure 4:
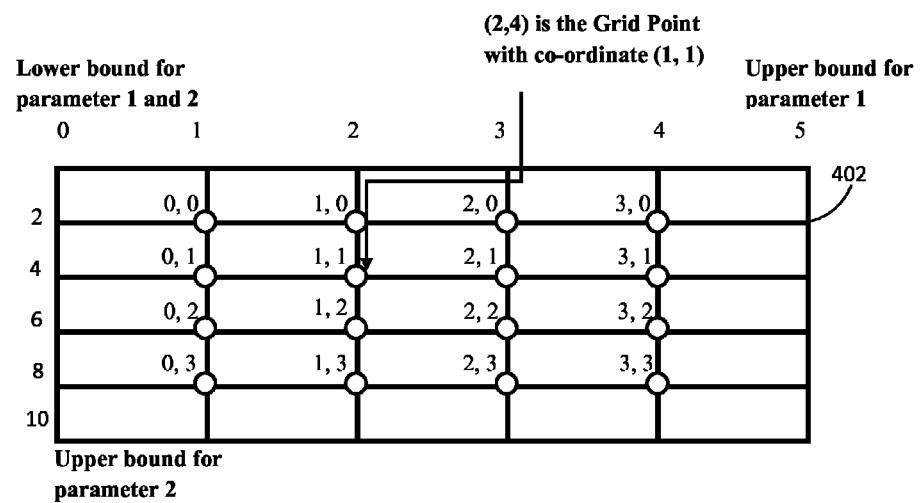
FIG. 4 (a) illustrates a creation of grid points in a parameter space based on the number of parameters and number of chosen grid points, in accordance with an embodiment of the present disclosure.
Figure 4:
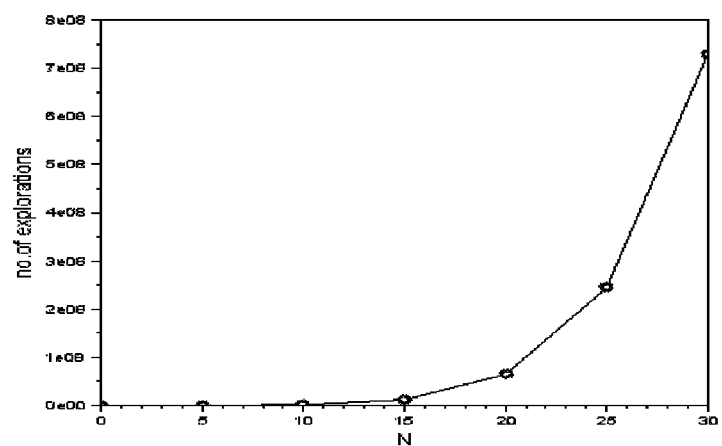

Referring to the FIG. 4 (a), let us understand the parallel implementation of the grid search technique for searching PK-PD parameters with a following example. In a first step, the receiving module 210 of the system 102 may receive a number of grids (N) induced over a parameter space 402, number of parameters (p), lower bound value (LBi) and upper bound value (UBi) of each parameter. In this example, the number of grids i.e., N is equal to 4 and the number of parameters i.e., p is equal to 2. Also, the lower bound value (LBi) for parameter 1 and 2 is equal to "0", whereas, the upper bound value (UBi) for the parameter 1 and the parameter 2 is "5" and "10" respectively.

Further, the determining module 212 of the system 102 may determine total number of grid points (n) based upon the number of grid (N) and the number of parameters (p) by using $n = N^p$. Thus, according to the present example, the total number of grid points (n) can be determined as "$n = N^p$" i.e., $n = 4^2 = 16$. Further, each grid point, of the total number of grid points, may be separated from the next grid point by a step size as shown in below equation:

$$\frac{(UB_i - LB_i)}{N + 1} \qquad (4)$$

Where, the $UB_i$ and the $LB_i$ are the upper bound value and the lower bound value of the parameter 'i' in whose direction the step is taken. Further, each grid point of the total number of grid points may be represented by a set of coordinates as shown in the FIG. 4 (a).

According to embodiments of the present disclosure, the computing module 214 of the system 102 may compute grid points corresponding to its coordinates based upon the lower bound value (LBi), the upper bound value (UBi), and the number of grids (N). Further, the computing module 214 performs the computation by using following formulae:

$$LB_i + (r_i + 1)\frac{(UB_i - LB_i)}{N + 1} \qquad (5)$$

Where '$r_i$'=0, 1, 2 ... N−1, i=0, 1, 2 ... (p−1) and (x, y) (where both x and y=0, 1, 2 ..., N−1) indicates the coordinate values for the grid point. As can be observed from the FIG. 4(a), the grid point computed for each of the coordinates are {(1,2), (1,4), (1,6), (1,8), (2,2), (2,4), (2,6), (2,8), (3,2), (3,4), (3,6), (3,8), (4,2), (4,4), (4,6), and (4,8)}. After computing the grid points for each of the coordinates, the next step is to compute an objective function value. The computing module 214 of the system 102 may be further enabled to parallelly compute an objective function value for each grid point of the plurality of grid points by using following equation:

$$WSRS = \sum_{i=1}^{\# \ Observations} w_i (y_{observed}^{(i)} - y_{predicted}^{(i)})^2$$

Wherein, $y_{observed}^{(t)}$ is observed value of dependent variable and $y_{predicted}^{(t)}$ is predicted value of the dependent variable.

Further, the computing module 214 may compare the objective function values (i.e., current objective function values) amongst each other in order to identify a grid point having a minimum or least objective function value. Further, the grid point identified to have minimum objective function value indicates the PK-PD parameters. Further, the parallel implementation of the above discussed grid search method on different hardware configurations are described in more detail in subsequent paragraphs of the specification.

Thus, we have already discussed above that the basic grid search algorithm may comprise iterating over all the grid points in the total number of grid points and calculating the objective function value (WSRS). Thereafter, selecting a grid point having the least objective function value as an optimum point. It may be observed that since the total number of grid points to be searched is $n=N^p$, therefore as N increases, there may be exponential rise in the number of points to be searched. This exponential rise may be seen in the FIG. 4 (b). Therefore, the system 102 is enabled to reduce the computational time for the grid search technique for large number of grid points such as 50, 100, 200, and the like. In one embodiment, the system 102 may be employed to test the performance of the grid search technique based on serial/sequential algorithm implementation. For implementing the grid search technique, the system 102 may be configured to have hardware of following specifications.

In one implementation, an Intel Sandybridge machine may be utilized having configurations comprising a 2.6 GHz Intel CPU, 16 physical cores, 32 cores with Intel HT technology, and 64 GB RAM. In another implementation, the machine having a Cluster with 64 nodes, 3 GHz Intel Clovertown CPU, 8 cores, 8 GB RAM, and a Message Passing with OpenMPI 1.6.3 may be utilized. In yet another implementation, Intel Xeon Phi Coprocessor (MIC) with 60 physical cores, 240 logical cores, and hosted on Intel Sandybridge machine may be used. In yet another implementation, two Nvidia GPUs of type C2075 Tesla GPU, having 5 GB RAM and hosted by 4-core Intel Xeon at 2.93 GHz may be used. The Intel Sandybridge CPU may be more powerful than the cluster CPUs which are based on earlier generation Intel clovertown architecture. The MIC (Many Integrated Core) and GPU (Graphics Processing Unit) architectures have many cores although each core is much less powerful.

As disclosed above, the grid search technique may be based on sequential/serial algorithm, wherein the objective function value may be computed corresponding to each grid point. Then based upon the objective function value computed, a grid point having minimum objective function value may be used for obtaining a set of parameters. Further, in the next iteration, another set of parameters may be obtained by adding a step size (as defined in equation 4) to one of the set of parameters. For example, considering the set of parameters computed corresponds to coordinate values (0, 0 . . . 0). Then the next set of parameters may be obtained by adding a step size to one of the parameters, starting with the rightmost parameter (parameter corresponding to the rightmost coordinate). The loop which is a do-while loop iterates till all the grid points in the grid have been searched. In one embodiment, the original code for the sequential algorithm was written in Java. The original code may be ported to C/C++ and performance may be measured for the number of grids N=20. Table I below illustrates the performance of the sequential algorithm.

TABLE I

Performance of Sequential code/program

| | JAVA Code | GNU C Compiler (gcc) | Intel C Compiler (icc) |
|---|---|---|---|
| Execution Time (sec) | 153 | 77 | 41.7 |

As illustrated in table I above, since icc performed better as compared to gcc, the icc may be used for measuring performance In the computational domain, it is well known fact that Base-2 computations of transcendental functions are slightly faster than other bases. The first optimization may include converting natural exponentials (exp (.) in C) to base-2 exponentials (exp2(.) in C) based upon following equation:

$$e^x = 2^{x \cdot log_2 \cdot e} \qquad (6)$$

Here log 2e is a constant. The conversion from exp (.) to exp2 (.) costs an extra multiply operation which may outweigh the gain obtained from the conversion of exp (.). But if the call is made inside a loop and the multiplication can somehow be hidden, one can obtain better performance. With the above change, one can get a 3.7% improvement in performance (execution time reduces to 40.2 sec). Using some of the compiler options which improves floating point performance (possibly at the cost of accuracy, although there wasn't any significant change in accuracy up to 16 decimal points), the execution was still further, reduced up to 37.2 sec (10.89% improvement w.r.t the original code). The icc compiler may automatically enable vectorization when —O2 optimization flag is used. But from the compiler reports, it was noticed that some of the loops were not vectorized. The system 102 may use explicit compiler commands for vectorization (# pragma simd) at all possible places in the code, and obtain a slight improvement in performance. The execution time may be reduced to 36.8 sec (11.85% improvement w.r.t the original code). The performance of gcc compiled code was not as good as compared to icc compiled code. Originally gcc had taken 77 sec, although by enabling vectorization and faster floating point operations, the system 102 could obtain an execution time of 68.3 sec (11.29% w.r.t original code). Further it was observed that, when the code was compiled with gcc by linking the icc math library instead of the default GNU math library, the performance obtained for the gcc was same as that of the icc. Based upon the above analysis, the system 102 may be configured for using the icc in order to compile the code implemented for parallelized grid search technique which is hereinafter described in detail.

As discussed above with reference to the sequential algorithm, the parameter values for each of the iteration of the loop may be calculated by adding a step size to the parameter values in the previous iteration of the loop. It may be concluded that, such iterative based calculation approach may create dependency amongst the loop iterations. For implementing the parallel algorithm, the system 102 may adopt the calculation in a manner such that each of the iteration may be able to calculate the coordinate values for the grid points and the corresponding set of parameter values independent of previous iterations. Such adoption may be enabled by substituting the "do . . . while loop" in the sequential/serial algorithm by a "for loop". It may be observed that the do-while loop is executed $N^p$ times. Therefore, for N=20 and p=6, number of iterations will be 64 000000. While parallelizing the grid search, the system 102 may map each value of the "for loop" iteration variable (say k) to one of the points in the grid, as illustrated in one example as below:

K = 0 -> (0, 0, 0, 0, 0, 0)

K = 1 -> (0, 0, 0, 0, 0, 1)

⋮

K = 19 -> (0, 0, 0, 0, 0, 19)

K = 20 -> (0, 0, 0, 0, 1, 0)

K = 21 -> (0, 0, 0, 0, 1, 1)

⋮

K = 64000000 -> (19, 19, 19, 19, 19, 19)

In one embodiment, the mapped coordinates may correspond to the p-digit base-N equivalent of the corresponding decimal number k. In the present case, since the number of parameters p=6, a six digit base-N number corresponding to k may be obtained. Inside the "for loop", the system 102 may calculate the point coordinates from the iteration variable 'k' using long division method. From the point coordinates, the system 102 may calculate the set of parameters using equation 5. It may be observed that computing the minimum of the objective function value across the grid points in the grid (or loop iterations) may limit the parallelization as it is a reduction operation. The parallelization of grid search technique may be enabled in various implementations including shared memory, distributed memory, and on specific hardware such as the GPU and the MIC. The various implementations are hereinafter described in detail as below.

Shared Memory Implementation

Figure 5:
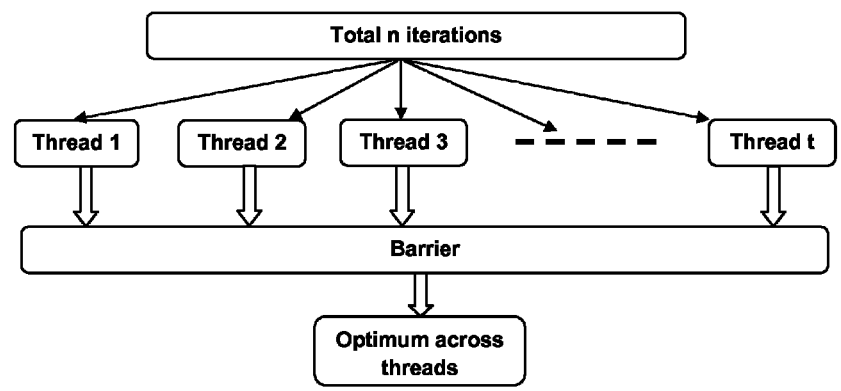
FIG. 5 (a) illustrates a parallel grid search technique using OpenMP, in accordance with an embodiment of the present disclosure.
Figure 5:
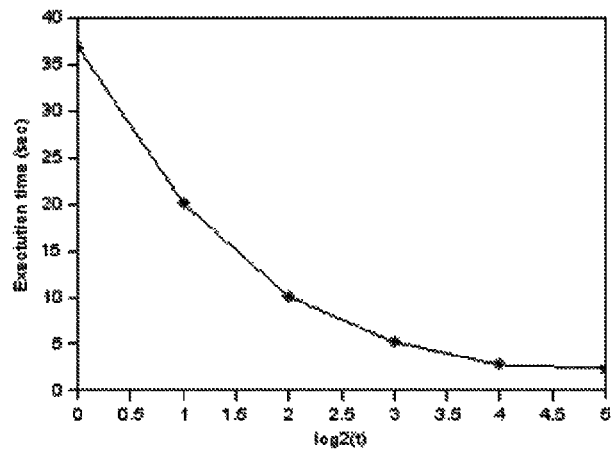

The system 102 may use OpenMP (i.e., Open Multi-Processing) for the shared memory parallel implementation of grid search. The OpenMp is a set of APIs that may be used for the shared memory parallel programming. The OpenMP is open source platform and easy to parallelize a software program/code. The details of the OpenMP has been described in OpenMP Architecture Review Board, "Openmp application program interface, Specification," 2011 available on http://www.openmp.org/mp-documents/OpenMP3.1.pdf and in a publication titled "Using OpenMP: Portable Shared Memory Parallel Programming (Scientific and Engineering Computation) by B. Chapman, G. Jost, and R. v. d. Pas published by The MIT Press, 2007. In one embodiment, the parallelization of the grid search code with OpenMP may comprise dividing the total number of loop iterations 'n' among the number of threads available. Each thread then may process a chunk of points and calculate the optimum within the chunk. After all the threads are finished with the processing of their local chunks, the optimum across the threads may be calculated. The shared memory parallel implementation of grid search is shown in FIG. 5 (a). In one exemplary embodiment, assume there are t threads, and each thread gets assigned (n/t) points. The OpenMP may automatically assign iterations to threads depending on the specified scheduling. In this embodiment, the system 102 may use static scheduling in which the iterations are mapped to threads equally at compile time. The performance of the OpenMP code may be measured on the Intel Sandybridge machine, results of which are shown in table II.

TABLE II

Performance of OpenMP Code

| No. of threads (t) | 1 | 2 | 4 | 6 | 16 | 32 |
|---|---|---|---|---|---|---|
| Execution Time (sec) | 36.8 | 20.12 | 10.1 | 5.2 | 2.8 | 2.4 |
| Speed Up | 1x | 1.8x | 3.6x | 7.1x | 13.1x | 15.3x |

Further, FIG. 5 (b) illustrates a plot of the execution time with the x-axis (no. of threads t) on log scale. Computing the optimum across the threads is serialized, but from measurement it is seen to take only a few milliseconds even with 32 threads. The performance does not scale much from 16 to 32 threads. In this embodiment, the machine had only 16 physical cores, 32 cores may be obtained by hyper threading so that each physical core runs two threads. Since the application is completely compute-bound (lots of computation and very little memory operations), the two threads on the single physical core utilizes the registers and other compute units to the fullest resulting in some contention, which is why the scaling is minimal.

Distributed Memory Implementation

Figure 6:
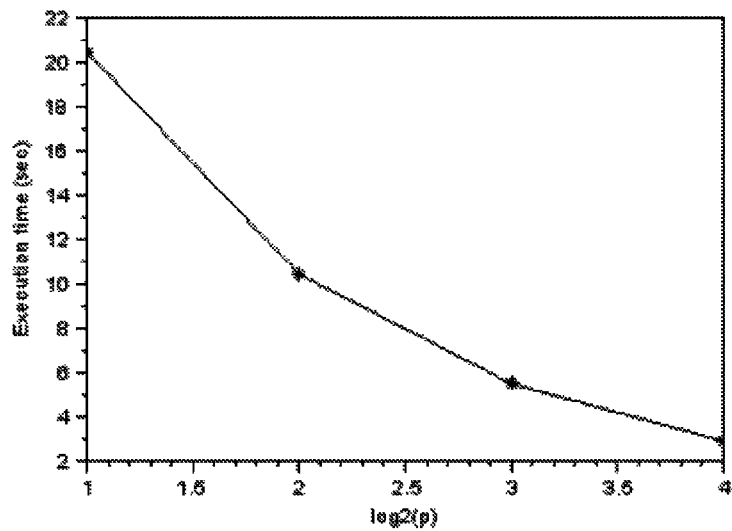
FIG. 6 (a) is a graphical plot illustrating performance of the grid search technique implemented using a MPI processes, in accordance with an embodiment of the present disclosure.
Figure 6:
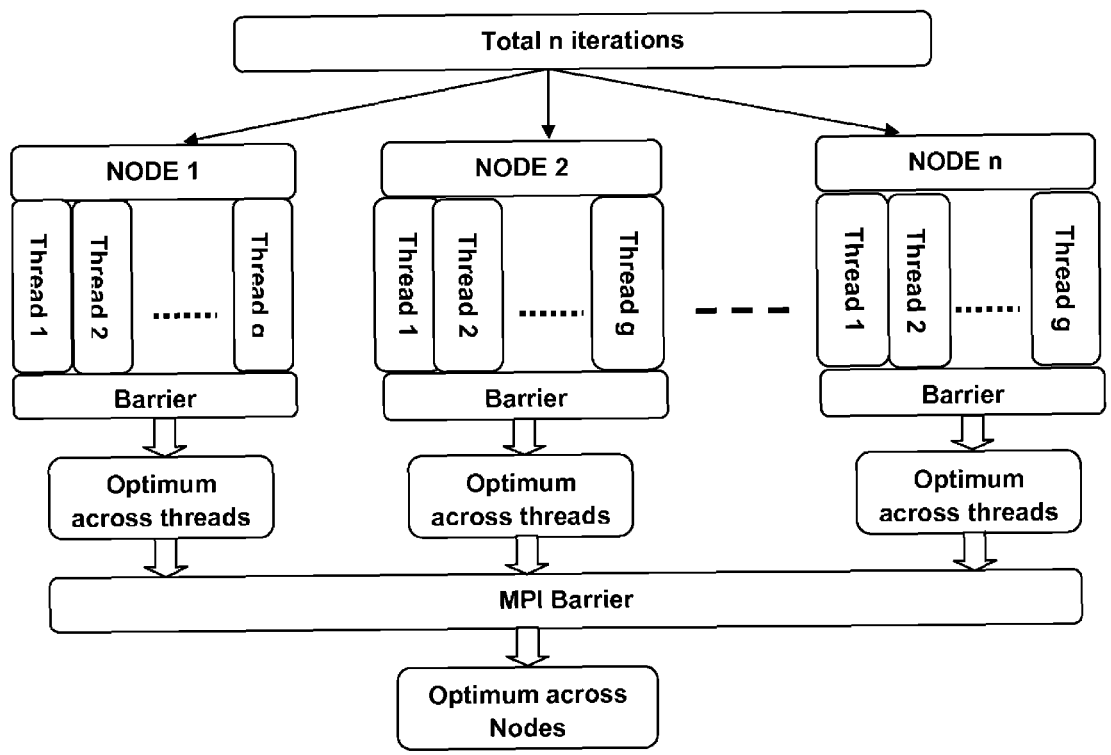

The system 102 may use Message Passing Interface (MPI) for the distributed memory implementation of the parallelization of the grid search technique. The MPI is a message passing library standard for parallel computers. There are several implementations of MPI and the system 102 disclosed herein use the OpenMPI implementation version 1.6.3 as described in a publication titled "Open MPI: Goals, concept, and design of a next generation MPI implementation," by E. Gabriel et. Al published at Proceedings, 11th European PVM/MPI Users' Group Meeting, Budapest, Hungary, September 2004, and another publication titled "The Architecture of Open Source Applications" volume 2 published by J. M. Squyres in April 2012. While the shared memory implementation may allow to do multithreading within a node, the distributed memory implementation may allow to parallelize the application across nodes. The computation is very similar to that of shared memory implementation. Each MPI process may process a chunk of points and provide a minimum objective function value. After all the processes are finished, one of the nodes may compute the minimum across the processes. The results obtained corresponding to the MPI on a single node are in illustrated in table III as below and in a plot as shown in FIG. 6(a). As illustrated in FIG. 6 (a), y-axis represents the execution time and x-axis represents the number of MPI processes p in log-scale.

TABLE III

Performance of MPI Code on a single node

| | No. of MPI Processes (p) | | | |
|---|---|---|---|---|
| | 2 | 4 | 8 | 16 |
| Execution Time (sec) | 20.47 | 10.45 | 5.5 | 2.9 |
| Speed Up | 1.79x | 3.52x | 6.69x | 12.68x |

Multinode Implementation

Figure 7:
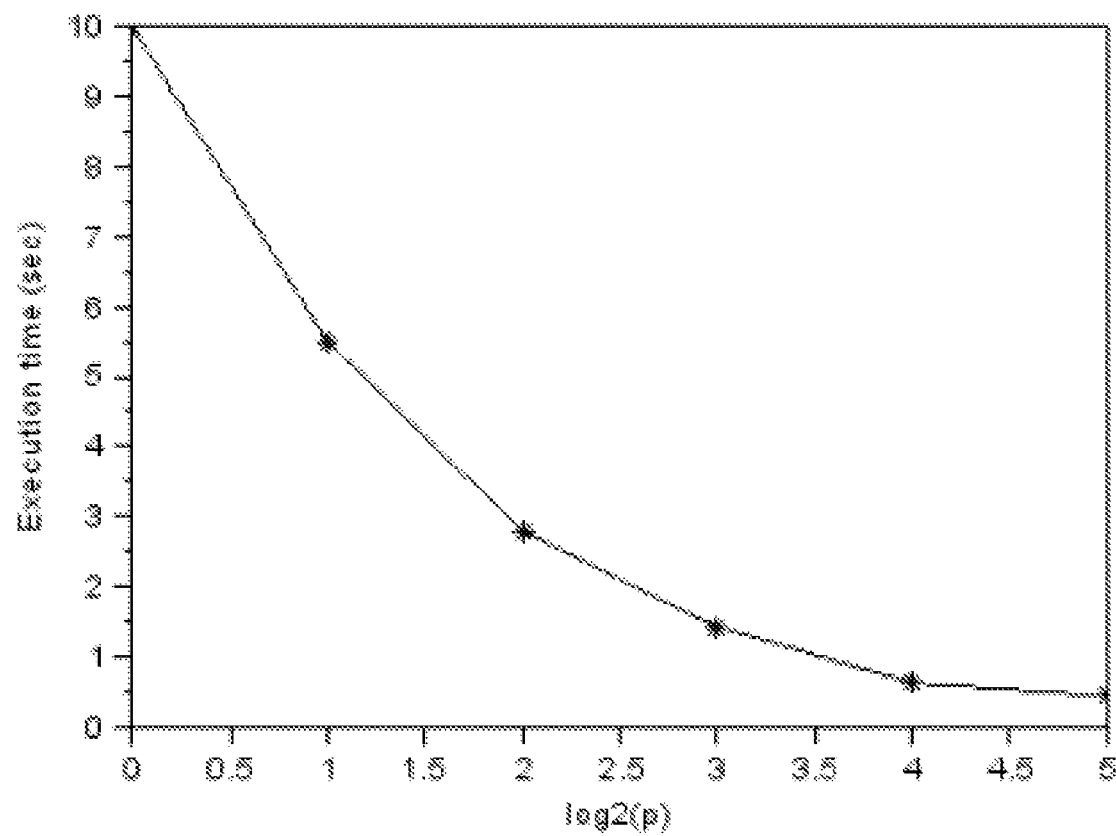
FIG. 7 (a) is a graphical plot illustrating performance of the grid search technique implemented using MPI-OpenMP computation, in accordance with an embodiment of the present disclosure.
Figure 7:
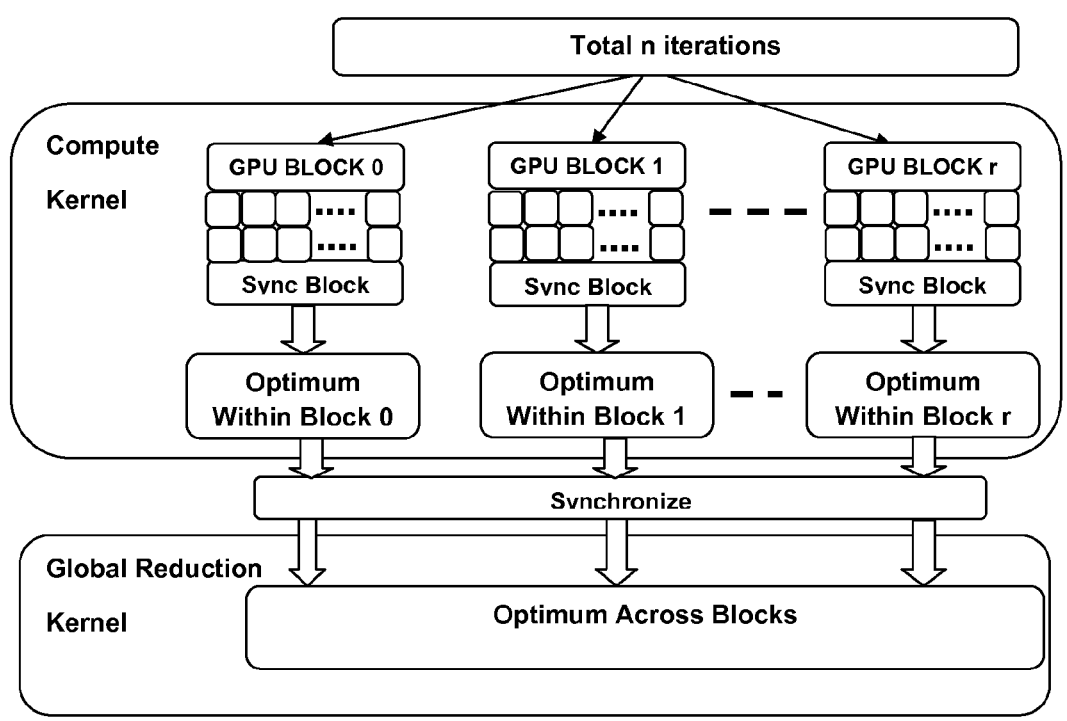

In one embodiment, the system 102 may be configured to improve the computational performance of the grid search technique by implementing MPI code on multiple nodes instead of a single node. The multimode implementation is shown in FIG. 6 (b). The performance of OpenMP code may be slightly better than that of MPI on a single node. The system 102 may use OpenMP within a single node. MPI may be needed for spreading the computation across nodes. Thus, the proposed approach may be considered to be a hybrid, wherein one MPI process may be spawned per node and each node use OpenMP for further parallelization within the node. The results are shown in table IV as below and in a plot as shown in FIG. 7 (a). As illustrated in FIG. 7 (a), y-axis represents the execution time and x-axis represents the number of nodes n in log-scale.

TABLE IV

Performance of MPI-OpenMP Code on multiple nodes

| Nodes (n) | 1 | 2 | 4 | 8 | 16 | 32 |
|---|---|---|---|---|---|---|
| Execution Time (sec) | 10 | 5.5 | 2.8 | 1.43 | 0.63 | 0.44 |
| Speed Up | | 3.68x | 6.69x | 13.14x | 25.73x | 58.41x | 83.63x |

In the multimode implementation, runs/executions may be made on a cluster with Intel Clovertown CPUs which are less powerful than the Sandybridge CPU on which the single node run may be made. Each cluster CPU may have 8 cores and 8 threads may be spawned on each node for computation using OpenMP as shown in FIG. 6 (b). On 32 nodes, the execution time may be reduced to 440 milliseconds. With 50 grid points on 32 nodes, the system 102 could run the algorithm in 78.9 seconds which is a significant improvement as compared to the serial code which would have taken 2-3 hours. With 64 nodes, the execution time for 50 grid points observed was 44.2 seconds.

Parallelization on the Graphical Processing Unit (GPU)

In one embodiment, the system 102 may implement parallelization of the grid search technique on Nvidia GPU using a Compute Unified Device Architecture (CUDA). In the CUDA programming model, the kernel is a function which is called from the host to execute on the GPU device. The execution of the kernel may be done by using a number of GPU threads. All the threads may execute the same code defined by the kernel. The GPU threads may be divided into a number of blocks (called grid), where each block contains a specific number of threads (Threads per block). The number of blocks along with the number of threads per block determine total number of threads launched by the kernel based upon following equation:

Total Number of Threads=No. of blocks×Threads per block (7)

In this embodiment, each thread may be assigned with a unique index within the block and each block may also be assigned with a unique index. The GPU may consist of a number of Streaming Multiprocessors (SMs), each of which contains a number of cores, along with other units such as schedulers and floating point units. The system 102 may use Nvidia Tesla C2075 GPU (Reference: "Nvidia tesla: A unified graphics and computing architecture" by E. Lindholm published in IEEE conference in March 2008) consisting of 14 SMs. Each SM may contain 32 cores resulting into a total of 448 cores. A block of threads may be executed inside one SM and each SM may execute a number of blocks, depending on the number of block size as well as the resources shared by the blocks. Resources available to an SM may be shared by the blocks executing on the SM. Threads within a block may have access to shared memory, which can be accessed only by the threads of that block. The execution of threads in a block may be divided into warps. A warp may refer to a set of threads which execute concurrently in a lock-step. On the Tesla C2075, the warp size is 32. The details on Compute Unified Device Architecture (CUDA) are described in a publication titled "CUDA by Example: An Introduction to General-Purpose GPU Programming", 1st ed. Published by Addison-Wesley Professional, 2010.

In this embodiment, for implementing the parallelization of the grid search, the system 102 may divide the computation among the GPU threads. Each thread may be assigned a number of grid points in the grid. The system 102 may calculate the objective function values for each of the grid points in the grid and then determine the optimum amongst the number of grid points. The system 102 may then calculate the optimum within each block. In the next step, the system 102 may launch another kernel which may calculate the optimum across blocks. The process is shown in FIG. 7 (b). The calculation of optimum across threads or blocks may be a reduction operation and may use shared memory which is fast and shared by threads within a block. The system 102 may define another variable called WORK PER THREAD indicating the number of grid points in the grid computed by each thread. The system 102 may then choose the variables such that, $$\text{WORK\_PER\_THREAD} \times \text{THREADS\_PER\_BLOCK} \times \text{NO\_BLOCKS} \geq n = N^p \quad (8)$$

In one embodiment, the system 102 may be configured for implementing several optimizations in order to facilitate the execution of the parallelization of the grid search technique. One of the optimizations facilitated by the system 102 may include implementing parallel reduction across multiple blocks. The application may require the computation of the objective function at all the grid points which is highly parallel, and then may require a reduction operation which may calculate a minimum across all the grid points. The reduction operation is not entirely parallel, and it may be optimized resulting in O(log 2(n)) performance for reduction. The whole computation may be carried out in two steps with two kernels. First step may be to perform the objective function computation on the grid points. The same kernel may compute the minimum of the objective function (reduction) across the grid points allocated to a GPU block. The second step may involve a kernel which may compute the minimum across the blocks (reduction) to get the final output. Reduction steps in both the kernels may therefore be optimized.

Another optimization facilitated by the system 102 may include optimizing dynamic memory allocations inside the kernel. The initial code ported to CUDA had an execution time of 46 seconds. By analyzing the code and through the use of the Nvidia Profiler (nvvp), the system 102 was able to determine a bottleneck to be the dynamic memory allocations inside one of the device functions. These may be removed by changing the declarations to be static and associating a corresponding functions into the body of the calling function. Once these are removed, the execution time may be reduced to 0.5 seconds. The reason for the speedup may be that dynamic allocations always allocate global memory as opposed to local memory on the GPU which is generally used with local function variables.

In this embodiment, another optimization facilitated by the system 102 may include reducing register spillage by optimizing the variables declared. Some of the variables declared inside various functions are redundant and may be removed. Since each thread in the GPU has limited amount of register memory (e.g. 64 in present case), using large number of variables may cause the register memory to overflow into other non-local memory resulting in register spillage. Optimizing the declared variables may result in reducing the spillage from around 30 bytes to zero bytes. Further, the execution time may reduce from 0.5 seconds to 0.47 seconds.

Another optimization facilitated by the system 102 may include choosing appropriate Grid size and Block size. In this embodiment, it was noted after rerunning the algorithm several times that the particular values of THREADS PER BLOCK, NO BLOCKS and WORK PER THREAD did not affect the execution times significantly, except that they should satisfy equation 8. Using low values for WORK PER THREAD such as 8 or below may lead to increase in execution time. Also, using a large value for WORK PER THREAD such as 512 or above may lead to a slight increase in execution time. In this embodiment, runs/executions may be made with THREADS PER BLOCK=64, NO BLOCKS=32768 and WORK PER THREAD=32.

Yet another optimization facilitated by the system 102 may include removing shared memory bank conflicts. The shared memory in GPU may be organized in banks and when two threads try to access memory in the same bank, a conflict occurs and the access is serialized. The system 102 may observe and/or monitor bank conflicts in the grid search algorithm and remove these by changing the access pattern of one of the shared arrays.

Another factor to consider while programming with CUDA may include the occupancy. The occupancy may give the ratio of the number of threads scheduled in an SM to the maximum number of threads that can be scheduled (depends on the particular GPU model). The occupancy observed is 33.3% and is limited by the number of registers in the Streaming Multiprocessor (SM) used by each thread. There is little scope of further improving the occupancy, and from a performance point of view increase in occupancy need not provide an improvement in execution time.

Yet another optimization facilitated by the system 102 may include optimizing arithmetic operation in CUDA. It is known that single precision operations are much faster on the GPU as compared to double precision operations. This is because, the SMs may have larger number of single precision floating point units available. By changing the exponential function call from the double precision to the single precision, there may be a substantial improvement in performance without compromising in accuracy of the results. It may be observed that, by implementing optimization of the arithmetic operation in the CUDA, the execution time may be reduced from 0.47 seconds to 0.19 seconds.

Figure 8:
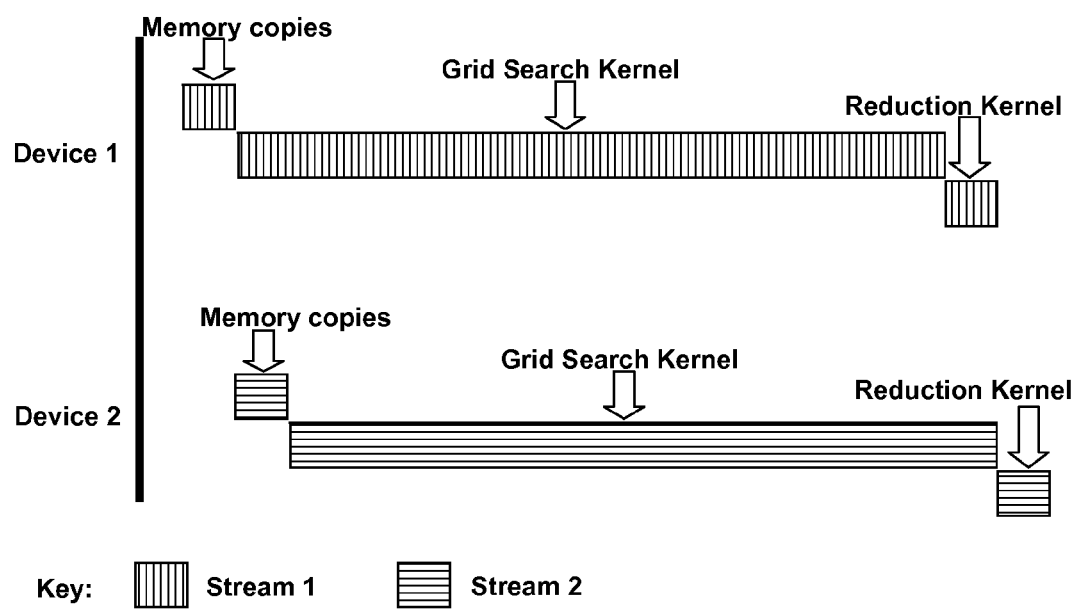
FIG. 8 illustrates comparative analysis of grid search computations using a single GPU and multi-GPUs, in accordance with an embodiment of the present disclosure.

Yet another optimization facilitated by the system 102 may include implementing multiple GPU approach. Specifically, in one embodiment, the system 102 may spread the computation to two GPUs. According to embodiments of present disclosure, the two GPUs may reside on the system 102. The system 102 may utilize streams available in the CUDA in order to split the computation among the GPUs. A stream is a set of tasks which execute serially on the GPU and is identified by a stream number. The system 102 may define the two streams and divide the total points in the grid among the two streams. Each stream may call the kernels and compute the optimum for its set of points. The optimum from among the streams may be determined after each stream completes. FIG. 8 illustrates performance of the system implementing the two GPUs for computing the parameters using grid search in accordance with one embodiment of the present disclosure. With the two GPUs, the execution time may be reduced to 0.092 seconds. i.e., the performance may increase two-fold. With 'n' number of GPUs available, the performance may increase n-fold. Table V below illustrates results on GPU running for N=20. Speed up shown is with respect to serial code on Intel Sandybridge machine. With grid points N=50, the execution time with two GPUs goes down to 22 seconds. It must be understood by one skilled in the art that results illustrated in table V is associated with the performance of the grid search technique utilizing two number of GPUs, however, the present disclosure is not limited to implementation of the grid search technique using one or two GPUs, and the present disclosure may be extended to utilize 'n' number of GPUs, wherein the performance will increase linearly with the number of GPUs utilized.

TABLE V

Performance of GPU Code

|  | 1 GPU | 2 GPUs |
| --- | --- | --- |
| Execution Time (sec) | 0.18 | 0.092 |
| Speed Up | 204x | 400x |

Thus, the present disclosure may enable improvement in performance of the grid search technique after parallelization of the serial/sequential code. The parallelization may require modifying the serial code so as to avoid the dependencies among the loop iterations. Further, the disclosure may enable optimizations that can be done on the serial code and the parallel code to facilitate better performance. The parallel code may be implemented using OpenMP on a single node, MPI on the cluster, and on Nvidia GPU using CUDA. All these methods may provide substantial improvements over serial code. For example, the OpenMP code resulted in 15.3x performance improvement on a single node, whereas the MPI implementation provided 83.6x improvements on 32 nodes. The OpenMP code was tested on Intel Sandybridge CPU which is superior in performance to the CPU available in the cluster. A cluster with Sandybridge CPUs would provide an even better performance with MPI. With GPUs, an improvement of 204x and 400x was obtained respectively with one and two GPUs.

It is to be noted that by implementing parallelization of the grid search on the Nvidia Tesla C2075 GPU, the execution time is reduced from 0.47 to 0.5 seconds, 0.5 to 0.255 seconds, 0.255 to 0.239 seconds, and 0.239 to 0.092 seconds by performing the optimization operation including removing dynamic memory allocations, Multi-GPU code (2 GPUs), removing register spilling (2 GPUs), and optimizing arithmetic operation respectively. Further, when the parallelization of the grid search is implemented on Nvidia Kepler K20 GPU, the execution time is further reduced to 0.072 seconds. Further, the results obtained using different hardware configuration (including the Nvidia Tesla C2075 GPU and Nvidia Kepler K20 GPU) after implementing the parallelized grid search is depicted in table below.

| Stages/Hardware Configurations | High Performance Computing (HPC) | Speedup (w.r.t serial code) |
|---|---|---|
| Serial Code for Grid Search method for 20 Grid Points (JAVA) (32 cores with HT Enabled, Intel Xeon@2.6 GHz, 64 GB RAM | 153 secs | — |
| After porting code into C (GCC) (32 cores with HT Enabled, Intel Xeon@2.6 GHz, 64 GB RAM) | 77 secs | 2 X |
| With openMP implementation on Xeon using 32 threads (32 cores with HT Enabled, Intel Xeon@2.6 GHz, 64 GB RAM) | 2.4 secs | 63.5 X |
| With MPI on 16 nodes/servers, each node/server have 1 MPI rank with 8 openMP Threads on EKA cluster (8 cores Intel Xeon @3 Ghz per node, 8 GB RAM) | 0.63 sec | 243 X |
| With MPI on 32 nodes/servers, each node/server have 1 MPI rank with 8 openMP Threads on EKA cluster (8 cores Intel Xeon @3 Ghz per node, 8 GB RAM) | 0.44 sec | 348 X |
| With CUDA implementation on 2 GPU (Tesla C2075) device | 0.092 sec | 1664 X |
| With CUDA implementation on 2 GPU (Nvidia Kepler K20) | 0.072 sec | 2125 X |

It is to be noted to a person skilled in art, that the example discussed in above paragraph and the table are associated with one case study. The timings (execution time) will change from one case study to another. From the different case studies it is observed that CUDA implementation on 2 GPU (Nvidia Kepler K20) is best combination.

Figure 9:
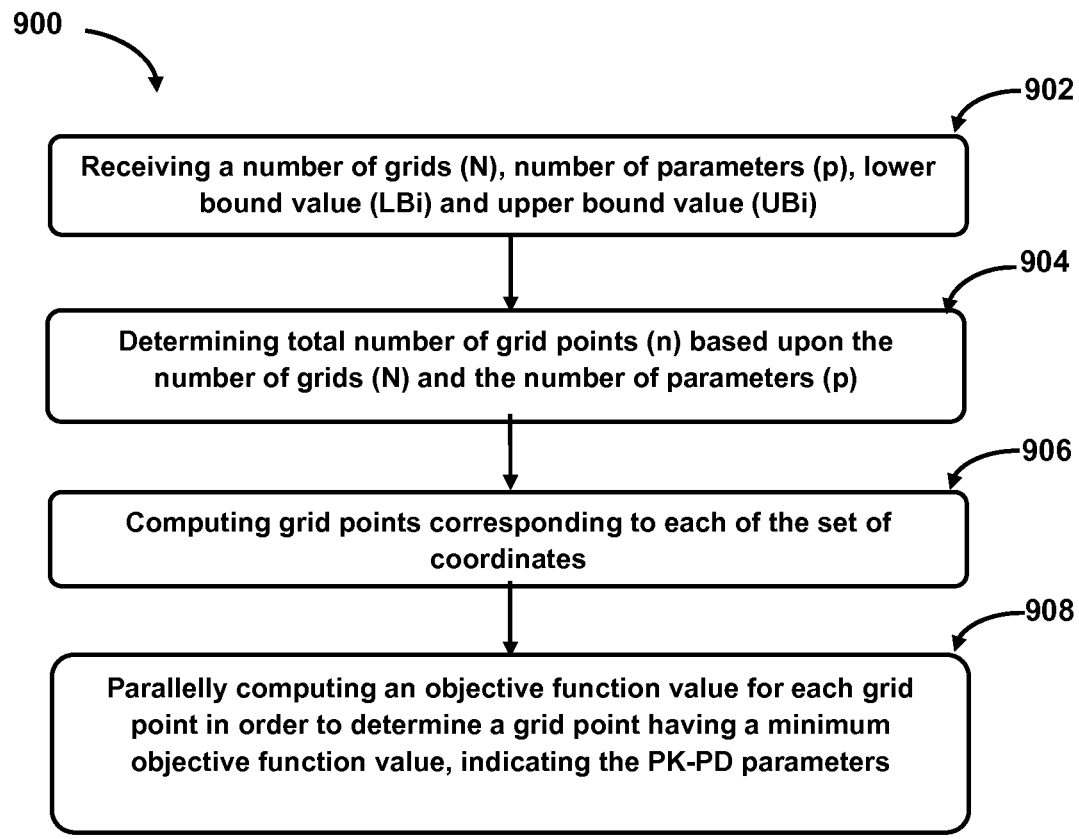
FIG. 9 illustrates method for searching the PK-PD parameters in a parameter space, in accordance with an embodiment of the present subject matter.

Referring now to FIG. 9, method for searching PK-PD parameters is shown, in accordance with an embodiment of the present subject matter. The method 900 may be described in the general context of computer executable instructions. Generally, computer executable instructions can include routines, programs, objects, components, data structures, procedures, modules, functions, etc., that perform particular functions or implement particular abstract data types. The method 900 may also be practiced in a distributed computing environment where functions are performed by remote processing devices that are linked through a communications network. In a distributed computing environment, computer executable instructions may be located in both local and remote computer storage media, including memory storage devices.

The order in which the method 900 is described is not intended to be construed as a limitation, and any number of the described method blocks can be combined in any order to implement the method 900 or alternate methods. Additionally, individual blocks may be deleted from the method 900 without departing from the spirit and scope of the subject matter described herein. Furthermore, the method can be implemented in any suitable hardware, software, firmware, or combination thereof. However, for ease of explanation, in the embodiments described below, the method 900 may be considered to be implemented in the above described system 102.

At block 902, a number of grids (N) induced over a parameter space, number of parameters (p), lower bound value (LBi) and upper bound value (UBi) of each parameter may be received. Further, the number of grids (N) determined is either user-defined or a predefined number, based on range of the parameters.

At block 904, a total number of grid points (n) may be determined based upon the number of grids (N) and the number of parameters (p). Further, each grid point, of the total number of grid points, is separated from an adjacent grid point based upon a step size. Further, each of the total number of grid points (n) is represented by a set of coordinates.

At block 906, plurality of grid points corresponding to the set of coordinates associated therewith may be computed based upon the lower bound value (LBi), the upper bound value (UBi), and the number of grids (N).

At block 908, an objective function value is parallelly computed for each of the total number of grid points. Further, a grid point having minimum number of objective function value, indicates the PK-PD parameters.

Although implementations for methods and systems for parallelizing grid search technique facilitating determination of PK-PD parameters have been described in language specific to structural features and/or methods, it is to be understood that the implementations and/or embodiments are not necessarily limited to the specific features or methods described. Rather, the specific features and methods are disclosed as examples of implementations for parallelizing grid search technique facilitating determination of PK-PD parameters.

We claim:

1. A method for searching Pharmacokinetic (PK)-Pharmacodynamic (PD) parameters in a parameter space, wherein the method comprising:
   receiving, by a processor, a number of grids (N) induced over a parameter space, number of parameters (p), lower bound value (LBi) and upper bound value (UBi) of each parameter;
   determining, by the processor, total number of grid points (n) based upon the number of grids (N) and the number of parameters (p), wherein each grid point is separated from an adjacent grid point based upon a step size, and wherein each of the total number of grid points (n) is represented by a set of coordinates;
   computing, by the processor, plurality of grid points corresponding to the set of coordinates associated therewith based upon the lower bound value (LBi), the upper bound value (UBi), and the number of grids (N);
   employing a parallelized grid search method based on the set of co-ordinates and initial PK-PD parameters to generate a plurality of final estimates for a parameter space;
   executing a parallel implementation of a grid search to automatically assign one or more iterations of the parallelized grid search method based on a specified scheduling; and
   parallelly computing, by the processor, an objective function value for each grid point of the plurality of grid points, wherein a grid point having a minimum objective function value indicates the PK-PD parameters.

2. The method of claim 1, wherein the number of grids (N) determined, is user-defined or a predefined number, based on the range of the parameters.

3. The method of claim 1, wherein the step size is determined by (UBi−LBi)/(N+1), wherein the UBi and LBi are upper bound value and lower bound value of parameter i, and N is the number of grids.

4. The method of claim 1, wherein the co-ordinate values is computed by using following equation: $LBi+(ri+1)(UBi-LBi)/(N+1)$, wherein the $ri=0,1,2,3, N-1$ and indicates co-ordinate values of the grid points.

5. The method of claim 1, wherein the PK-PD parameters are searched based on a model selected from a group comprising of a single compartmental model, a multi-compartmental model, an algebraic model, and a differential equation model.

6. A system for searching Pharmacokinetic (PK)-Pharmacodynamic (PD) parameters in a parameter space, the system comprises:
a processor;
a memory coupled to the processor, wherein the processor executes a plurality of modules stored in the memory, and wherein the plurality of modules comprises:
a receiving module to receive a number of grids (N) induced over a parameter space, number of parameters (p), lower bound value (LBi) and upper bound value (UBi) of each parameter;
a determining module to determine total number of grid points (n) based upon the number of grids (N) and the number of parameters (p), wherein each grid point is separated from an adjacent grid point based upon a step size, and wherein each of the total number of grid points (n) is represented by a set of coordinates; and
a computing module to:
compute plurality of grid points corresponding to the set of coordinates associated therewith based upon the lower bound value (LBi), the upper bound value (UBi), and the number of grids (N),
employ a parallelized grid search method based on the set of co-ordinates and initial PK-PD parameters to generate a plurality of final estimates for a parameter space;
execute a parallel implementation of a grid search for automatically assigning one or more iterations of the parallelized grid search method based on a specified scheduling; and
parallelly compute an objective function value for each grid point of the plurality of grid points, wherein a grid point of the plurality of grid points having a minimum objective function value indicates the PK-PD parameters.

7. The system of claim 6, wherein the number of grids (N) determined, is user-defined or a predefined number, based on range of the parameters.

8. The system of claim 6, wherein the step size is determined by (UBi−LBi)/(N+1), wherein the UBi and LBi are upper bound value and lower bound value of parameter i, and N is the number of grids.

9. The system of claim 6, wherein the co-ordinates is computed by using following equation: LBi+(ri+1) (UBi−LBi)/(N+1), wherein the ri=0, 1, 2, 3, N−1.

10. A non-transitory computer readable medium embodying a program executable in a computing device for searching Pharmacokinetic (PK)-Pharmacodynamic (PD) parameters in a parameter space, the program comprising:
a program code for receiving a number of grids (N) induced over a parameter space, number of parameters (p), lower bound value (LBi) and upper bound value (UBi) of each parameter;
a program code for determining total number of grid points (n) based upon the number of grids (N) and the number of parameters (p), wherein each grid point is separated from an adjacent grid point based upon a step size, and wherein each of the total number of grid points (n) is represented by a set of coordinates;
a program code for computing plurality of grid points corresponding to the set of coordinates associated therewith based upon the lower bound value (LBi), the upper bound value (UBi), and the number of grids (N);
a program code for employing a parallelized grid search method based on the set of co-ordinates and initial PK-PD parameters to generate a plurality of final estimates for a parameter space;
a program code for executing a parallel implementation of a grid search to automatically assign one or more iterations of the parallelized grid search method based on a specified scheduling; and
a program code for parallelly computing an objective function value for each grid point of the plurality of grid points, wherein a grid point having a minimum objective function value indicates the PK-PD parameters.

11. The method of claim 1, wherein the objective function value is computed by using following equation:

$$WSRS = \sum_{i=1}^{\text{\# Observations}} w_i (y_{observed}^{(i)} - y_{predicted}^{(i)})^2$$

wherein $y_{observed}^{(i)}$ is observed value of dependent variable, and $y_{predicted}^{(i)}$ is predicted value of the dependent variable.

12. The system of claim 6, wherein the objective function value is computed by using following equation:

$$WSRS = \sum_{i=1}^{\text{\# Observations}} w_i (y_{observed}^{(i)} - y_{predicted}^{(i)})^2$$

wherein $y_{observed}^{(i)}$ is observed value of dependent variable, and $y_{predicted}^{(i)}$ is predicted value of the dependent variable.

* * * * *